United States Patent [19]

Gardner et al.

[11] Patent Number: 4,459,191
[45] Date of Patent: Jul. 10, 1984

[54] LIGHT-CATALYZED PROCESS FOR PREPARING AMINES

[75] Inventors: David M. Gardner, Collegeville, Pa.; Richard V. Gutowski, Haddon Heights, N.J.

[73] Assignee: Pennwalt Corporation, Philadelphia, Pa.

[21] Appl. No.: 333,941

[22] Filed: Dec. 23, 1981

Related U.S. Application Data

[63] Continuation-in-part of Ser. No. 259,731, May 1, 1981, abandoned, which is a continuation-in-part of Ser. No. 143,989, Apr. 28, 1980, abandoned.

[51] Int. Cl.³ .............................................. B01J 19/12
[52] U.S. Cl. ............................ 204/158 R; 204/162 R
[58] Field of Search ...................... 204/158 N, 162 R

[56] References Cited

U.S. PATENT DOCUMENTS 3,491,008  1/1970  Broaddus ........................ 204/158 N Primary Examiner—Howard S. Williams

[57] ABSTRACT

Aliphatic and aromatic amines are prepared by the addition of N—H bonds from ammonia or a primary or secondary amine across the double bonds of an olefin under the influence of light energy, preferably in the presence of a photocatalyst. Amines are widely used commercially as intermediates in the manufacture of rubber products, pharmaceuticals, insecticides, dyestuffs, textile finishing agents, etc.

13 Claims, No Drawings

LIGHT-CATALYZED PROCESS FOR PREPARING AMINES

BACKGROUND OF THE INVENTION

This application is a continuation-in-part of copending application Ser. No. 259,731 filed May 1, 1981, now abandoned, which is a continuation-in-part of application Ser. No. 143,989 filed Apr. 28, 1980, now abandoned.

This invention relates to a method for preparing aliphatic and aromatic amines from olefins and ammonia or a primary or secondary amine. In particular, this invention is concerned with forming aliphatic, cycloaliphatic, heterocyclic aliphatic, or aromatic amines from an olefin and either ammonia or a primary or secondary amine by the catalytic use of actinic light.

PRIOR ART

Prior art methods for preparing amines have either involved reduction of nitriles, nitro compounds, etc. or have involved reactions in which the amino group replaces some other functional group, such as the hydroxyl group in alcohols, the chloro or bromo group in alkyl chlorides or bromides, the oxygen in the carbonyl group of aldehydes or ketones, or an alkoxy group in ethers. Direct synthesis of amines from olefins bypasses the need for these intermediate compounds containing functional groups and simplifies the isolation and purification of the desired product amines.

U.S. Pat. No. 2,772,271 discloses a method for reacting amines and alpha-olefins in the presence of peroxides or light that results in addition of the olefin at an alpha carbon atom of the amine. Similarly, U.S. Pat. No. 3,492,353 contains a disclosure of an analogous reaction in which the amine is trimethylamine and which is conducted in the presence of a free-radical catalyst or actinic radiation of a quartz discharge lamp (which emits above 2240 Å) This reaction likewise leads to addition of olefin molecules to the carbon atoms alpha to the amino nitrogen. D. Bryce-Smith et al. [*Angew. Chem., Int'l Ed.*, 13, 341 (1974)] reports 1,2- and 1,3- photoaddition of primary and secondary amines to benzene. F. D. Lewis and T. Ho [*JACS* 99, 7991 (1977)] and M. Kawanisi and K. Matsunaga [*J. Chem. Soc. Chem. Commun.* 313 (1971)] report the photochemical addition of dialkylamines to stilbene (an activated olefin) to form, among other products, N,N dialkyl-1,2-diphenylethylamine, but only in low yields (15–20%). The reaction of ammonia with benzene, toluene, or xylene under the influence of a nondisruptive electric discharge or irradiation by actinic light to form aniline, toluidine, and xylidine, respectively, plus hydrogen as disclosed in U.S. Pat. No. 2,749,297, does not involve addition across a double bond.

STATEMENT OF THE INVENTION

The present invention is directed to a process for producing aliphatic and aromatic amines comprising reacting a primary or secondary amine or ammonia with an olefin in the presence of
 light having a wavelength of above 1600 Å and a photocatalyst,
whereby an N—H bond of the amine or ammonia is added across the double bond of the olefin.

DISCUSSION OF INVENTION

The process of the present invention can be illustrated by the following general reaction:

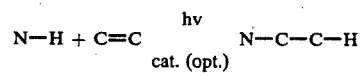

This process can be conducted both with or without a photocatalyst depending on the source of actinic radiation used. It has been discovered that if a suitable photocatalyst is not present, the light source must be one with significant output in the spectral region with wavelengths from about 2200 Å to about 1600 Å to be effective. Since the reactors and lamps used for this process usually consist of vessels having conventional quartz glass walls to pass actinic light, the lower-wavelength end, in practice, is usually set by the light transmission cut-off of conventional quartz glass (around 1800 Å). However, we have found that the use of amorphous silica or synthetic silica glass for the vessel walls or for the lamp glass of the equipment of this process is advantageous because it transmits more short-wave length ultraviolet radiation than conventional quartz glass (cut-off around 1600 Å). Glass comprising such synthetic silica is marketed under the trademark Suprasil ® by Heraeus Amersil and as Corning #7940 by Corning Glass Company.

Typical lamps emitting in the range of 1600–2200 Å are deuterium lamps, low-pressure mercury-argon lamps, and high-energy xenon flash lamps. The high-energy xenon flash lamp is particularly effective because of its high-energy intensity and its large output in the range 1800–2200 Å. This listing is non-limiting and the lamps mentioned are to be used only as examples of available light sources. Lamps that transmit light with wavelengths above this range are only marginally effective without the use of a photocatalyst; additionally, low-energy flash lamps which peak out at about 4000 Å, require the use of a photocatalyst to provide a suitable yield in this reaction.

As used herein, the term photocatalyst can mean a material which whan added to the reactants causes the desired reaction to occur under the influence of actinic light at a significantly increased rate. Although not wishing to be limited by any theory, the photocatalyst can be a light-absorbing organic compound, a transition-metal coordination compound that can complex with the olefin and amine reactants and make them more susceptible to reaction under the influence of actinic light, or mercury.

Useful organic photosensitizers fall into the categories of ketones, aromatic hydrocarbons, alcohols, organometallics heterocyclic amines, organic dyes, sulfur-compounds, and organo derivatives of Group V A elements. Examples of useful organic photocatalysts for this invention are acetone, 2-butanone, 2-pentanone, 3-pentanone, 4-heptanone, diisopropylketone, acetophenone, isobutyrophenone, propiophenone, benzophenone, 3-hydroxy-2-butanone, 2,4-pentanedione, benzene, m-xylene, diacetone alcohol, pyridine, 2,2'-diethoxyacetophenone, triphenylphosphine, triphenylarsine, triphenylbismuthine, triphenylstibine, tributylphosphine and 8-hydroxyquinoline. Preferred examples are acetone, 2-butanone, and 2,4-pentanedione.

Examples of suitable transition-metal complexes are coordination compounds of rhodium, ruthenium, iron and molybdenum. Specific examples are: hydridocarbonyltris (triphenylphosphine) rhodium (I), chlorotris (triphenylphosphine) rhodium (I), dichlorobis (dimethylglyoximato) rhodium (III), dichlorobis (phenylmethylglyoximato) rodium (III), methylaquobis (dimethylglyoximato) rhodium (III), chlorotriphenylphosphinebis (dimethylglyoximato) rhodium (III), dichlorotetrakis (isoquinolino) rhodium (III) chloride, dichlorotris (triphenylphosphine) ruthenium (II), hexamolybdenum dodecachloride, molybdenum (II) cluster compounds of the formuls $Mo_6Cl_{12}$, $[Mo_6Cl_8]$ $Cl_4L_2$, where L is a ligand displaceable by the amino reactant and may be the amino reactant (e.g., $(CH_3)_2$ NH or $NH_3$) itself, and Group VIII metal carbonyls. Preferred transition-metal photocatalysts are dichlorotris (triphenylphosphine) ruthenium (II), chlorotris (triphenylphosphine) rhodium (I), molybdenum (II) cluster compounds of the formula $[Mo_6Cl_8]$ $Cl_4L_2$ (when L is as defined above) and $Fe(CO)_5$.

The above photocatalysts can be used individually or in combination to improve conversions and yields. Particularly preferred are combinations of $Fe(CO)_5$ with one or more of the following compounds: tri(n-butyl) phosphine, tri(n-propyl) phosphine, triethylphosphite, diethylphenylphosphine, diphenylchlorophosphine, bis(1,2-diphenylphosphino) ethane, and 2,4-pentanedione.

Organic photocatalysts can be added in any catalytically effective amount with respect to the amine or ammonia reactant, with the preferred range being below the limit of solubility of the organic photocatalyst. Transition-metal photocatalysts may also be added in any effective amount, but are typically used at their solubility limits in the ammonia or amine reactants.

Mercury is usually employed as a catalyst in a vapor form prepared by passing an inert carrier gas, e.g., helium, through elemental mercury maintained at vaporization temperature (200° C.). Fine droplets of elemental mercury may also be used without a carrier, if desired. The mercury catalyst is used in an amount at least sufficient to demonstrate catalytic activity. The maximum concentration of mercury which is used with an inert carrier is up to and including the amount of mercury vapor carried by the flowing gas at the saturated vapor-pressure of mercury.

Suitable reactants containing N—H bonds are ammonia and the various primary and secondary amines. Specific examples of such amines include: methylamine, dimethylamine, ethylamine, dimethylamine, n-propylamine, isopropylamine, di(n-propyl) amine, di(isopropyl) amine, n-butylamine, di(n-butyl) amine, sec-butylamine, di-(sec-butyl) amine, isobutylamine, di(isobutyl) amine, the pentyl and higher alkyl amines; cycloaliphatic amines such as cyclohexylamine; aromatic amines such as aniline, the N-alkylanilines, diphenylamine, the naphthylamines, and the toluidines; heterocyclic amines such as pyrrolidine, morpholine, and piperidine; substituted amines such as the alkanolamines; and polyamines such as ethylene diamine, and 1,6-hexanediamine.

Preferred N—H containing reactants, because of their commercial significance, are ammonia, and the mono- and di-alkyl ($C_1$-$C_6$) amines. An especially preferred N—H containing reactant is ammonia.

Olefinic compounds suitable for the present process include those having one or more non-aromatic carbon-carbon double bonds, internal and/or terminal. Specific examples of such compounds are ethylene, propylene, 1-butene, 2-butene, isobutylene, 1-pentene, 2-pentene, 3-methyl-1-butene 2-methyl-1-butene, 2-methyl-2-butene, the several possible hexenes, higher alkenes (e.g., dodecene), cyclobutene, cyclopentene, cyclohexene, cycloheptene, stilbene, styrene, alpha methylstyrene, alpha, alpha-dimethylstyrene, cyclopentadiene, cyclohexadiene, cyclooctadiene, butadiene, 2-methyl-1,3-butadiene, 2-chloro-1,3-butadiene, cyclododecatriene, acrylonitrile vinylchloride, methyl vinyl ether, allyl alcohol, and furan.

Double bonds adjacent to groups that can stabilize free-radicals are said to be activated, and these generally react much more readily than unactive double bonds.

Preferred olefins for our process, because of their commercial significance, are the unactivated alkenes of 2 to 8 carbons having terminal double bonds.

It is to be understood that the N—H containing reactants and olefins can be optionally substituted with various groups (such as —OH, -halide, —CN) as long as such groups do not interfere with the process.

Typical temperatures for conducting the process of this invention range from $-10°$ C. to $40°$ C. but any convenient temperature may be used. Temperatures in the range $-10°$ C. to $10°$ C. are preferred. The lower temperatures allow greater solubility of gaseous olefins, such as ethylene, in liquid ammonia or the amines.

The mole ratio of ammonia or starting amine to olefin can range from 1:1 to 20:1 with a ratio in the range of 5:1 to 15:1 being preferred.

Although it is preferable to conduct the reaction of this invention in the liquid phase, it is also possible to operate in the gas or solid phase. By operating in the gas phase the use of certain solid photocatalysts may be precluded because of their low vapor-pressure.

EXAMPLES

Most of the examples which follow, illustrate the process of this invention as carried out in an apparatus which can be used in a continuous process in either the liquid or gas phase using known methods for introducing reactants and the photocatalyst, and for separating products from the starting materials.

EXAMPLE 1

18.2 moles of ammonia was charged into a reactor system consisting of a one-liter stainless steel reservoir, a quartz reactor for admitting the actinic light to the solution, and a circulating pump. External to the quartz reactor was an ultraviolet light source. Both reactor and light source were enclosed in a reflecting stainless steel cylinder. Ethylene was then charged into the system until the pressure reached 260 psig and 2.3 moles of ethylene were dissolved in the ammonia. Before the lamp was turned on, the solution was circulated for approximately one-half hour to ensure proper mixing and to cool the reactant mixture to $7°$–$8°$ C. No reaction was observed in this period. The circulating high pressure (autogenous) liquid reactant mixture was then exposed to ultraviolet lamps for the time periods given in Table 1. Analyses of the final mixture by gas chromatography are also shown in the Table. Conversations are given for ethylene, and yields are to mixed mono-, di- and tri-ethylamines. The high-energy xenon flash lamp of Table 1 discharges 25 joules over a 10 cm. path through a 1 mm. bore; the spectral output peaks at 3000 Å and a large proportion of the radiation falls in the range of 1800–2200 Å.

TABLE 1

| LAMP | EXPOSURE TIME (HRS) | % CONV. | % YIELD |
|---|---|---|---|
| a. 550W Hg | 4.0 | 5.3 | 5 |
| b. Hg - Ar | 4.0 | 15.1 | 39.7 |
| c. Deuterium | 4.0 | 6.9 | 68.5 |
| d. High-Energy Xenon Flash | 0.5 | 8.1 | 79.1 |
| e. Low-Energy Flash | 4.0 | 0 | 0 |

It is readily seen from Table 1 that poor yields are obtained with the mercury lamp, a device that has no output below 2200 Å, and the low-energy xenon flash lamp which discharges 25 joules over a 10 cm. path through a 13 mm. bore and has a spectral output peak of 4000 Å.

EXAMPLE 2

A mixture of 18.2 moles of ammonia and 0.9 moles of acetone was charged into the reactor system described in Example 1. Ethylene was then charged into the system and 2.3 moles dissolved in the ammonia-acetone solution. After circulation of the solution for one-half hour, a deuterium lamp was turned on and the solution exposed for 4 hours. Analysis of the final mixture by gas chromatography showed a 27.9 conversion of ethylene with a 72.1% yield to mono-, di- and tri-ethylamines.

EXAMPLE 3

A mixture of 18.2 moles of ammonia, 1.82 moles of 1-butene and 0.9 moles of acetone was charged into the reactor system described in Example 1 except that the light source was 550-watt mercury lamp. The high-pressure liquid mixture was circulated for four hours at 8° C. Gas chromatographic analyses and confirmatory identifications by mass spectrometry showed a 7.0% conversion to N-ethyl-n-butyl amine. When acetone is not used, no product is observed.

EXAMPLE 4

A mixture of 17.0 moles of ammonia, 1.72 moles of 1-octene, and 0.88 moles of acetone was charged into the reactor system described in Example 1 and circulated for five hours at 8° C. The UV light source was a 550-W mercury lamp. The product, 2.9 grams of octylamine, was collected at 180° C. by distillation and identified by NMR. Further confirmation was obtained by titrimetric analysis. When acetone is not used, no product is observed.

EXAMPLE 5

A mixture consisting of 8.68 moles of ethylamine, 1.43 moles of 1-butene and 0.7 moles of methyl ethyl ketone was charged into the reactor system described in Example 1. Circulation of this reactant mixture for four hours at 8° C. gave a 1-butene conversion of 5.0% and yield to N-ethyl-n-butylamine of 100% using the 550-W mercury lamp.

EXAMPLE 6

A mixture of 5.0 moles of n-butylamine, 0.5 mole of acetone and 0.84 mole of ethylene were charged into the reactor system described in Example 1. Circulation of the reactant mixture for four hours at 8° C. using the 550-Watt mercury lamp gave a conversion of ethylene of 12.0% and a yield to N-ethyl-n-butylamine of 100%.

EXAMPLE 7

A mixture of 7.60 moles of dimethylamine, 1.15 moles ethylene and 0.0023 mole of $Mo_6Cl_{12}$ was charged into the reactor system described in Example 1. Circulation of the reactant mixture for four hours at 8° C. gave a conversion of ethylene of 10% and a combined yield to dimethylethylamine, diethylmethylamine, and triethylamine of nearly 100% using the 550-watt mercury lamp.

EXAMPLE 8

A mixture of 4.04 moles of n-butylamine, 0.221 mole of $Fe(CO)_5$, and 0.221 moles of triethyl phosphite was pressurized to 250 psig, at 35° C., with ethylene in the reactor system described in Example 1. The light source was a 550 watt, high pressure mercury ultraviolet lamp. The mixture was circulated for 4 hours with constant irradiation. Analysis of the products showed a 15.5% conversion of the n-butylamine to N-ethyl-n-butylamine.

EXAMPLE 9

Ammonia (18.2 moles) and ammonium chloride ($NH_4Cl$, 0.18 mole) were charged to a 1-liter cyclic system equipped with a circulating pump, a cooling coil, and a cylindrical glass reactor. An ultraviolet lamp was mounted near the reactor and both the reactor and lamp were enclosed in a reflecting stainless-steel cylinder. Ethylene was charged to the system until the pressure was, arbitrarily, 250 psig. The resulting solution was circulated for about ½ hour or until the solution temperature reached 7°-8° C. The lamp was turned on and the solution was irradiated for four hours.

To demonstrate the influence of amorphous silica glass in the reactor and the irradiating lamp, the results of eight runs using the above described procedure are reported in the following table. In four (4) of the eight runs, the reactor walls were of conventional quartz glass while in the remaining four (4) runs, the reactor walls were of amorphous silica glass (Suprasil ®). In both series of four (4) runs, the irradiating lamps of two (2) runs had conventional quartz glass housings while the other two (2) used lamps with amorphous silica glass Suprasil ® housings. The percent conversions in the table are based on the amount of ammonium chloride present since, in every case, the product, ethylamine, was obtained as the corresponding hydrochloride. The yields are virtually quantitative.

TABLE 2

| | Conversions to Ethylamine Lamp Type | | | |
|---|---|---|---|---|
| Reactor Wall | Hg. Quartz[a] | Hg. Amorphous[a] Silica | Xe Quartz[b] | Xe Amorphous[b] Silica |
| Quartz | <1% | 40% | 30% | 40% |
| Amorphous Silica | 10% | 100% | 100% | 100% |

[a] 550 watt, high pressure mercury lamp
[b] high intensity xenon flash lamp.

EXAMPLE 10

Gaseous ammonia, ethylene, helium and mercury vapor are exposed simultaneously to ultraviolet light in a single-pass reactor system consisting of flow controllers, a stainless-steel, mercury-reflux pot and a quartz reactor chamber. A stream of helium is first passed through elemental mercury heated to about 200° C. and the He/Hg vapor is immediately blended with a mixture of ethylene and ammonia (1:1 volume) prior to the reactor chamber. The reactor chamber is irradiated by a low-pressure mercury lamp external to the reactor. The vent gases were collected and the product was identified as ethylamine in 85 to 98% purity.

We claim:

1. A process for producing amines comprising reacting a primary or secondary amine or ammonia with an olefin in the presence of light having a wavelength of above 1600 Å and a photocatalyst which is stable to U.V. light, whereby an N—H bond of the amine or ammonia is added across the double bond of the olefin.

2. The process of claim 1 wherein the reaction is carried out in a reactor vessel having amorphous silica glass walls.

3. The process of claim 1 wherein said light has a wavelength ranging up to 4000 Å and the photocatalyst is mercury, a light-adsorbing organic compound, a transition-metal complex, or a combination thereof.

4. The process of claim 3 wherein the organic compound is a ketone, an aromatic hydrocarbon, an alcohol, an organometallic, a heterocyclic amine, an organic dye, a sulfur compound, or an organo derivative of Group V A elements.

5. The process of claim 3 in which the photocatalyst is a coordination compound of rhodium, ruthenium, iron, or molybdenum.

6. The process of claim 3 where the photocatalyst is dichlorotris (triphenylphosphine) ruthenium (II), chlorotris (triphenylphosphine) rhodium (I), $Mo_6Cl_{12}$, a molybdenum cluster complex of the formula $[Mo_6Cl_8]Cl_4L_2$ where L is a ligand displaceable by the amino reactant, or $Fe(CO)_5$.

7. The process of claim 3 wherein the photocatalyst is a combination of $Fe(CO)_5$ with one or more of the following compounds: tri(n-butyl) phosphine, tri(n-propyl) phosphine, triethylphosphite, diethylphenylphosphine, diphenylchlorophosphine, and bis (1,2-di-phenylphosphino) ethane.

8. The process of claim 1 wherein said light has a wavelength ranging up to 4000 Å the N—H containing reactant is ammonia or a mono- or di-alkylamine where the alkyl groups have 1 to 6 carbons.

9. The process of claim 8 wherein the olefin is an alkene having 2 to 18 carbons.

10. The process of claim 9 wherein the alkene has a terminal double bond and 2 to 8 carbons.

11. The process of claim 10 wherein the photocatalyst is selected from the group consisting of acetone, 2-butanone and 2,4-pentanedione.

12. The process of claim 10 wherein the photocatalyst is selected from the group consisting of dichlorotris (triphenylphosphine) ruthenium (II), chlorotris (triphenylphosphine) rhodium (I), $Mo_6Cl_{12}$, $[Mo_6Cl_8]Cl_4L_2$ where L is a ligand displaceable by the amino reactant, and $Fe(CO)_5$.

13. The process of claim 11 or 12 wherein the reaction is carried out in a reactor vessel having amorphous silica glass walls.

* * * * *